United States Patent [19]

Saxena

[11] Patent Number: 4,676,898

[45] Date of Patent: * Jun. 30, 1987

[54] CHROMATOGRAPHY COLUMN USING HORIZONTAL FLOW

[75] Inventor: Vinit Saxena, Pinole, Calif.

[73] Assignee: Sepragen Corporation, San Leandro, Calif.

[*] Notice: The portion of the term of this patent subsequent to Dec. 9, 2003 has been disclaimed.

[21] Appl. No.: 869,295

[22] Filed: Jun. 2, 1986

Related U.S. Application Data

[63] Continuation-in-part of Ser. No. 794,727, Nov. 4, 1985, Pat. No. 4,627,918.

[51] Int. Cl.⁴ .............................................. B01D 15/08
[52] U.S. Cl. .................................. 210/198.2; 210/656
[58] Field of Search ...................... 210/635, 656, 198.2

[56] References Cited

U.S. PATENT DOCUMENTS 4,627,918 12/1986 Saxena .............................. 210/198.2

Primary Examiner—Ernest G. Therkorn
Attorney, Agent, or Firm—Shyamala T. Rajender

[57] ABSTRACT

A chromatographic column is disclosed in which flow through the separating medium bed takes place horizontally. The column is packed with small, rigid, high performance separation medium. The fluid sample containing several components flows horizontally through the stationary phase or medium and is separated at least partially into discrete components. Means for providing even horizontal flow distribution of the sample fluid and for collection of the discrete components of the sample fluid are included. The stationary phase consists of a packed bed of high performance, small size particles of either (a) absorbants such as silica, alumina etc; (b) packing for reverse phase ion-exchange, affinity, hydrophobic, chiral or ion chromatography; (c) hydroxylapatite; or packing used for desalting. The column as a whole may be fabricated to be disposable or may be constructed to have a more simplified but durable housing.

24 Claims, 6 Drawing Figures

CHROMATOGRAPHY COLUMN USING HORIZONTAL FLOW

RELATED APPLICATION

This application is a continuation-in-part and improvement over the invention described and claimed in copending application Ser. No. 794,727 filed Nov. 4, 1985, now U.S. Pat. No. 4,627,918.

This invention relates to chromatography systems, particularly to an improved chromatography system utilizing horizontal flow through the separating medium, and more particularly to a horizontal flow analytical and preparative column for high performance chromatography.

BACKGROUND OF THE INVENTION

Chromatograpny, as it is generally used, is a technique used for the separation of various components of a "sample" mixture. In a liquid chromatography system, a sample followed by an elution fluid are injected into a separation column. The separation column contains a packing or matrix medium or material, as well known in the art, which interacts with the various components of the sample fluid to be separated. The composition of the separating medium depends on the fluid being directed therethrough so as to produce the desired separation. The separation columns generally known in the art are of a cylindrical construction and the fluid flows axially through a separating medium bed (packing or matrix) retained in the column. The medium bed is retained between supports or frits on either or both ends of the column. As the sample and elution fluids pass through the separating medium bed, the constituents of the sample fluid travel at different rates due to their interaction with the matrix or packing material. As a result, these constituents emerge separated (i.e., have different elution times) in the outlet stream of the column.

These prior known approaches are exemplified by the following U.S. Patent No. 3,230,167 issued Jan. 18, 1966 to M. J. E. Golay; U.S. Pat. No. 3,422,605 issued Jan. 21, 1969, to R. P. Crowley; U.S. Pat. No. 3,453,811 issued July 8, 1969, also to R. P. Crowley; U.S. Pat. No. 3,780,866 issued Dec. 25, 1973 to L. V. Ek et al; U.S. Pat. No. 4,133,562, issued Jan. 9, 1979 to L. H. Andren; U.S. Pat. No. 4,350,595 issued Sept. 21, 1982 to W. Gunkel; U.S. Pat. No. 4,354,932 issued Aug. 19, 1982 to R. J. McNeil; and U.S. Pat. No. 4,496,461 issued Jan. 29, 1985 to G. Leeke et al.

In the case of conventional chromatography, the available matrices or separation material beds for separating substances of large molecular weight are soft and compress easily. Matrix compression in turn causes dramatically reduced flow through the separation column. When chromatographic separation systems are scaled up for commercial purposes, more matrix volume is required and thus larger columns have to be employed. Additionally, the process requires a substantial increase in the fluid flow rate to achieve acceptable production rates. The combination of high flow rates and larger bed height (i.e., hydrostatic head) results in high pressure drops across the matrix that in turn further compress the matrix material, adversely affecting flow through the column. Some prior designs have addressed this problem by incorporating short, wide columns; i.e., columns with large cross-sectional area and reduced height. While this prior design does help reduce pressure drops and improve throughput, the geometry results in large saucer shaped (center dipping) columns when additional scale up is desired. Larger diameter columns have the problems of: (1) inconvenient geometry for fabrication, (2) difficulty in even packing of the column, (3) uneven distribution of the sample over the cross-sectional area, and (4) large dead volume leading to loss in chromatographic resolution. Due to these problems, scale up is often accomplished by using multiple columns in parallel or using larger columns but with smaller diameter-to-height ratios. The first alternative mentioned above can be cumbersome and often results in high costs while the second alternative leads to a recurrence of the problem with compression of the matrix or separator material bed. The process has to be reoptimized since the flow rates have to be altered to reduce pressure drop, leading to considerable expense in terms of time and material.

High performance chromatography, on the other hand, has confronted the problems of low flow rates and poor resolution by the use of small size (range of 3-60 um) column packings made from inert, rigid column supports such as silica, glass, polymers, hydroxylapatite, metals etc. The rigid supports are designed to withstand pressures of the order of several thousand psi.

Traditionally, high performance liquid chromatography (HPLC) has been carried out in a manner very similar to conventional chromatography. The column packings are compressed in a long, narrow bed between two bed supports or frits inside a long, narrow column. The sample is applied to the top of the bed and interacts with the packing material in one of a variety of ways such as ion-exchange, absorption, affinity, adsorption, hydrophilic or hydrophobic interactions and by other mechanisms known to those skilled in the art. The degree ano strength of the interaction varies with the type and nature of the packing material and the components of the sample mixture. Thus, when an "eluant" which also interacts with the sample, is passed through the bed, each of the components of the sample mixture dissociates differently, travels down the column at different rates and are thus differentially eluted. The concentration of each component in the effluent or eluant stream may be determined by measuring the amount of a detectable component or label contained in the sample fluid by methods known in the art, which include but is not limited to absorption or emission spectrometry in the uv, visible or infra red range, measurement of the refractive index, radioactivity, fluorescence tagging and the like.

High performance liquid chromatography has been applied to separating complex mixtures, often with components with very similar physical and chemical properties. This nas generally been possible because of the very small size particles used in HPLC. The small particle size of the separating medium gives rise to a large surface area in a given volume which allows for a high degree of surface interactions. This high degree of surface interactions in turn results in low height equivalent per theoretical plate (HETP) and high efficiency high performance separations.

This form of chromatography has been, as discussed earlier, carried out in long, narrow bore columns. The combination of long bed height, and small particle size with high flow rates gives rise to an enormous back pressure which varies from about 50 psi to 5000 psi. These high back pressures drastically limit the choice of preferred column packings. Furthermore, especially in the separation of larger, labile biomolecules, there is a risk of these sheer sensitive proteins or macromolecules being denatured by the high pressures generated. Finally and most importantly, special packing materials, special pumps, special mixers, special injectors and other associated instrumentation designed to withstand these high pressures have had to be developed and utilized. While HPLC enjoys wide spread use because of its high separation potential, especially of closely related compounds, the need for the development of specialized materials and equipment has driven up the price of the column packings, HPLC components and equipment as well as integrated systems.

Efforts to scale up HPLC from an analytical mode to a preparative level require high flow rates and high capacities and have necessitated increasing the column height. This in turn has resulted in even higher back pressures which have proved to be impractical to handle. Widening the column bore has resulted in other types of problems such as uneven distribution of the sample over the entire cross section of the bed and channelling or tunnelling along the wall of the column. These result in decreased resolution, reduction in column capacity and an over all decrease in operating performance. New sample and eluant distributors to overcome uneven distribution, and radial-pak columns to minimize the channelling effect, have been designed and tested. However, the problems associated with difficult scale-up, high flow rates, resulting high back pressures and exorbitant price tags for preparative HPLC are wide spread and are of enormous concern especially as the emerging biotechnology companies scale up production levels.

The above mentioned problems have led to the search for economical column packings which would lower pressure drops, for example, spherical silica-based supports, monodispersed polymeric beads etc. Some of these efforts, including new and different columns, are exemplified by the following patents.

U.S. Pat. No. 4,496,461 issued Jan. 29, 1985 to Leeke et al., and U.S. Pat. No. 4,512,897 to Crowder et al., disclose a unique column design in which fibrous-like packing material is immobilized on membrane sheets. The membrane sheet is spirally wound around a hollow core and is encased in a cartridge. The cartridge is in turn enclosed in a housing. Sample and eluant are introduced into the housing from outside the cartridge, flow through the spirally wound membrane and are collected and removed from the center core. The complex flow pattern, the swellable nature of the matrix and membrane material and the high dead volume results in considerable band broadening and poor separations.

The above design was then modified to a configuration where multiple doughnut shaped disks of membranes are stacked vertically inside the cartridge. This arrangement allows for fast flow and also limits expansion and contraction of the matrix and membrane materials, but the deal volume in the column remains significant, leading to low resolution in the chromatographic separation. Furthermore, the capacity of the column is limited by the nature, amount and size of the particles that could be effectively and efficiently immobilized on the membrane surface. Additionally, the membrane material normally used with these systems are generally unstable in organic solvents often used with HPLC. Thus, these columns are not suitable for application in HPLC.

The copending patent application referenced hereinabove, describes and claims a unique column using horizontal flow chromatography. This column which is described in the referenced patent application employs a design wherein sample fluid is introduced via a distributor to the outer circumferential wall of the bed, travels radially (or horizontally) in through the bed, which consists of packing material, where the components get separated and exit via the collection port in the center of the column. This horizontal flow column has a high cross sectional area and very low effective bed height. It thus offers the ability to handle very high flow rates at low operative pressures. Since the bed height remains constant even with scale up, the design offers the linear scale-up feature described in the above referenced application. However, the column described in the prior application, specifically the cylindrical embodiment has several drawbacks: (i) too high a dead volume for HPLC applications; (ii) no easy way to pack the column; (iii) no easy way to remove air once it is trapped in the system; (iv) materials of construction not suitable for HPLC applications; (v) too many turns in the distributor channels which would easily be plugged up with debris and would be difficult to clean; and (vi) cumbersome fabrication.

Therefore, it is an object of the present invention to provide a horizontal flow high performance chromatography column.

A further object of the invention is to provide an apparatus for high performance liquid chromatography (HPLC) which overcomes or reduces the above referenced drawbacks of the prior known horizontal flow chromatographic columns.

Another object of the invention is to provide an improved horizontal flow HPLC wherein the dead volume is reduced and the sample flow channels are simplified thereby eliminating or reducing the possibility of plugging.

Another object of the invention is to provide an improved horizontal flow chromatography column which is simplified in construction providing for easy packing of the column and removal of trapped air therefrom.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to an improved apparatus and a method for performing not only classical or conventional chromatography but also high performance chromatography in a horizontal mode with appropriate column configuration. As used herein, the terms "horizontal or radial flow or mode", which are used interchangeably, are defined as flow of the sample or eluant fluid through the chromatographic column in a direction that is perpendicular to the longitudinal axis of the column, regardless of the position of the column relative to the work bench or support stands or other equipment used to support or stack the columns.

This chromatographic separation in a horizontal mode may be accomplished by means of a chromatographic column constructed so as to have an inner and outer annuli, with the matrix material being packed therebetween. The bed height is thus computed as the distance between the inner and outer annuli. Chromatography consequently takes place radially in the column. Furthermore, horizontal flow may also be achieved in a cubic arrangement where the flow takes place between two vertically held end plates.

The column configuration of the present invention result in even bed height since the inlet and outlet distributors are fixed. The distributor and collection channels are designed to provide even application of the sample and horizontal streamlines across the chromatographic bed. The long, vertical column assembly with horizontal flow is easy to fabricate and convenient for packing and handling. Furthermore, since the bed height is constant along the length of the column, both the cross-sectional area and bed volume are proportional to the column length. Thus, scale-up is possible by linearly increasing the length of the column in proportion to the desired scale of operation. At any scale of operation, the pressure drop remains constant and scale up is accomplished easily by linear increments of the column bed length.

More specifically, the improved apparatus of this invention is particularly applicable to high performance chromatograpny used in conjunction with the separation of biomolecules or other organic or inorganic compounds. The invention provides an improved chromatographic column capable of use both in high performance and conventional chromatography, in the identification and separation of such mixtures in the analytical mode as well as providing scale-up to larger columns for use in the isolation of components from mixtures in quantities suitable for preparative or production purposes.

The apparatus of this invention, as exemplified by FIG. 1, provides the following advantages over the prior known columns:

(1) the dead volume is reduced by (a) making both frits flush with the solid core or the cylinder wall respectively and (b) machining fine grooves on the inner solid core to form the inner channel and machining fine grooves on the outside of the porous frit to form the outer channel;

(2) the ease of packing is facilitated by employing two fittings on the top flange, one to slurry pack the column and the other to remove any trapped air;

(3) a variety of materials such as, for example, stainless steel, aluminum, titanium, glass, teflon, polycarbonates, polysulfones, polypropylenes and the like, may be employed for the construction of the column body and other non-filter components to withstand solvent and temperature conditions normally employed in HPLC. Similarly, the frits may be constructed out of polypropylene, teflon, stainless steel, PVDF, polyacetate, polyesters, ceramics, and other porous materials;

(4) the distributor channels are machined to feed directly into the outer annular channel; and (5) the improved design also involves (a) making the solid core out of one piece and attaching it via threads to the bottom flange and (b) the elimination of O-rings used in the above referenced application.

Finally, the improved embodiments have also been scaled down to small size or semi-analytical levels in the form of a disposable radial-flow column.

BRIEF DESCRIPTION OF THE DRAWINGS

The accompanying drawings, which are incorporated and form a part of the specification, illustrate an embodiment of the invention and, together with the description, serve to explain the principles of the invention.

DETAILED DESCRIPTION OF THE INVENTION

Figure 1:
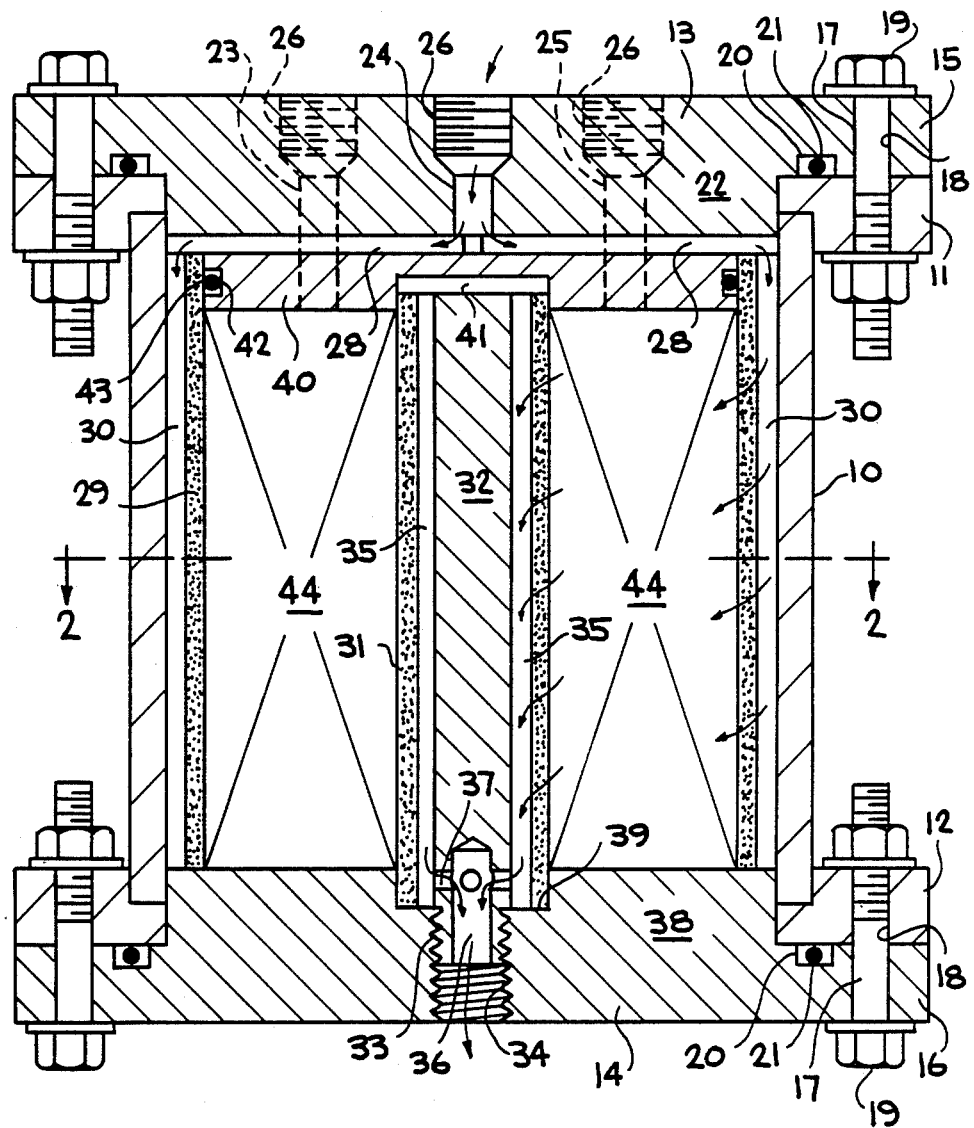
FIG. 1 is a cross-sectional view of an embodiment of the improved chromatography column in accordance with the invention.

The present invention involves an improved chromatography column utilizing horizontal flow of the sample and carrier medium or eluant material. As used herein, the terms "horizontal or radial flow or mode", which are used interchangeably, are defined as flow of the sample or eluant fluid through the chromatographic column in a direction that is perpendicular to the longitudinal axis of the column, regardless of the position of the column relative to the work bench or support stands or other equipment used to support or stack the columns. The column may be of a cylindrical or other configurations in the construction, with the flow of a sample fluid through a separating medium bed therein being in a horizontal direction. The column of this invention includes means for evenly distributing the flow, achieving horizontal streamlines, and collecting the separated components, while providing easy scale-up thereof for high volume operation. The column of this invention overcomes the problems associated with large diameter or length columns by: (1) providing a convenient geometry for fabrication; (2) ease of packing the column with separating medium; (3) even distribution of the sample matrix over the separating medium bed; and (4) low dead volume area. The column bed height of the cylindrical embodiment is given by the distance between inner and outer annuli, and thus can be scaled-up by increasing the length linearly, without any increase in pressure drop across the separating material bed.

Each embodiment utilizes a horizontal or radial fluid flow of the sample and the elution fluids through or across the separating medium bed, matrix, or packing retained within the column. Each embodiment utilizes a distribution system for the sample fluid which evenly distributes the sample fluid over the entire cross-sectional area of the bed, matrix or packing.

The improved chromatographic column of this invention involves both a horizontal flow analytical and a preparative column for high performance liquid chromatography (HPLC). As in the above-referenced application Ser. No. 794,727, now U.S. Pat. No. 4,627,918, flow through the separation medium bed is in a horizontal direction with respect to the vertical axis of the column. The direction of horizontal flow, as illustrated in the accompanying drawings, is radially inwardly, although it is within the scope of this invention to so design the distribution system to direct the flow radially outwardly through the separation medium.

For high performance applications, the separation medium bed is composed of small particles of:

(a) absorbants such as silica, alumina, carbon etc.;
(b) packings for reverse phase ion-exchange, affinity, hydrophilic, hydrophobic, chiral or ion chromatography;
(c) hydroxylapatite;
(d) packings used for desalting; or
(e) other HPLC packings known in the art.

The column as a whole, or at least the bed of separation medium, may be fabricated to be disposable. As will become more apparent from the accompanying drawings and the following description, the improved chromatography column provides the following advantages:

1. The dead volume is further reduced by (a) making both frits flush with the solid core or the cylinder wall respectively, and (b) machining fine grooves on the outer surface of the inner solid core to form the inner or collection channel and machining fine grooves on the outer surface of the outer porous frit to form the inlet sample fluid channel.

2. The ease of packing is facilitated by employing two fittings on the top flange or upper end of the housing, one to slurry pack the column and the other to allow for the removal of any trapped air.

3. A variety of material may be employed for the construction of the column body and other non-filter components to assure that such materials withstand solvent and temperature conditions normally encountered in HPLC, such materials being exemplified by stainless steel, teflon, aluminum, titanium, glass, polycarbonate, polysulfone, polypropylene, polypropylene, PVDF etc. Similarly, the filter frits may be made up of polypropylene, teflon, stainless steel, polyacetate, polyester, polycarbonate, ceramics and other porous materials.

4. The distributor channel is machined to feed the sample fluids directly into the outer annular channel adjacent the surface of the outer frit.

5. The improved structural arrangement also involves (a) making the solid inner core out of one piece and attaching it via threads to the bottom flange of the column housing and (b) the elimination of O-ring seals.

In addition, an embodiment of the column is scaled down to small size or semi-analytical levels in the form of a disposable radial flow column.

Referring now to the drawings, FIG. 1 illustrates a cylindrically constructed chromatography column in accordance with the invention. While the illustrated embodiment is of a cylindrical configuration, such is not intended to limit the invention to the particular configuration or to limit it to a specific shape or size. The column comprises basically, a housing having a cylindrical body section and upper and lower removable end sections; a centrally located core member having grooves spaced around the outer surface to form a collection or outlet channel; a pair of spaced porous tubular frits between which is retained a bed of selected separating medium, the outer of the pair of porous frits being provided with a plurality of spaced grooves on the outer surface thereof which function as fluid inlet channels which are in fluid communication with distributor channels located in the upper end section of the housing. The lower housing end section is constructed to retain the core member and is provided with a fluid passageway which cooperates with the grooves in the core member to remove the fluid components from the column.

One of the structural improvements provided by the column of this invention is in the grooves in the outer porous frit and the central core member which constitute the fluid flow channels. Another structural improvement is in the construction of the upper end section of the housing which provides for greater ease in inserting and removing the frits and the separation bed material while providing means for removing air from the column during packing of the bed. Thus, this arrangement facilitates the use of disposable separation beds and easy exchange of the beds as also entirely disposable columns.

Figure 2:
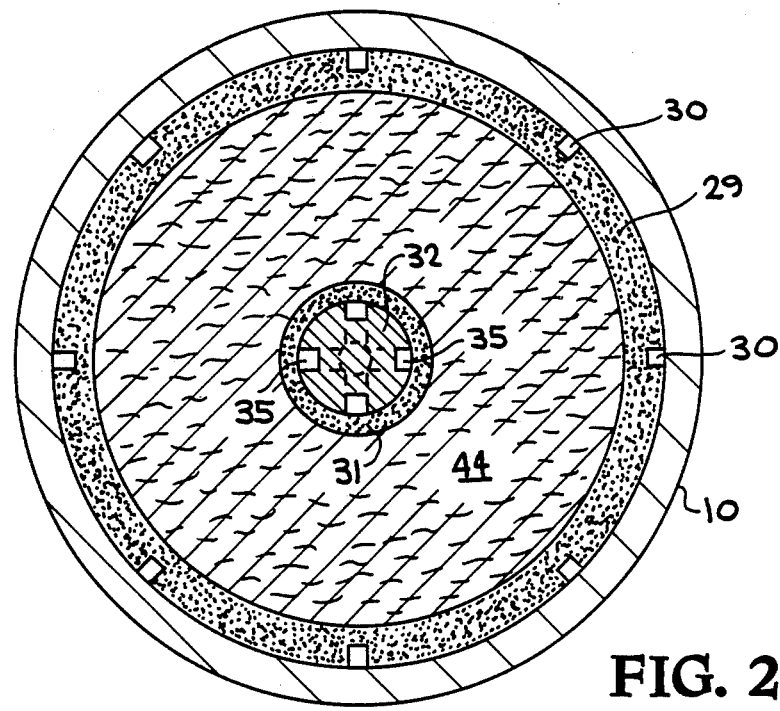
FIG. 2 is a view taken along the line 2—2 of FIG. 1 showing the flow channels.
Figure 3:
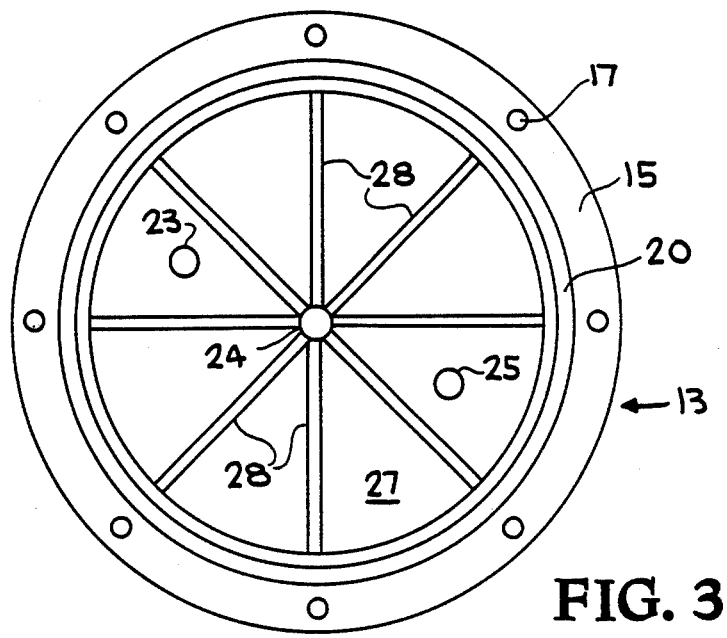
FIG. 3 illustrates the sample fluid inlet distribution system of the FIG. 1 embodiment.
Figure 4:
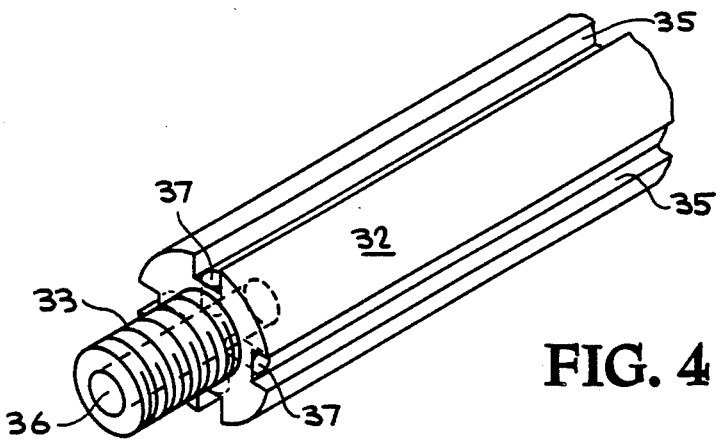
FIG. 4 is a perspective view of the central core member of the FIG. 1 embodiment.

Referring now to FIGS. 1-4, the column includes a housing consisting of a cylindrical or tubular body section 10 having flanges 11 and 12 on opposite ends, secured thereto as by welding, an upper end section or cap generally indicated at 13 and a lower end section or cap generally indicated at 14. Each of end sections 13 and 14 is provided with a peripheral lip 15 and 16, respectively, having apertures 17, which align with apertures 18 in flanges 11 and 12, through which bolts or other securing means 19 extend for removably securing end sections 13 and 14 to body section 10 of the housing. Each end section 13 and 14 is provided with eight apertures 17 (see FIG. 3) which align with apertures 18. (Although the embodiment of FIG. 3 is provided with eight apertures, the invention is not limited to eight apertures. There may be more or less than eight apertures utilized). To prevent fluid leakage between flanges 11 and 12 and end sections 13 and 14, the peripheral lips 15 and 16 are provided each with an annular groove 20 within which is located an O-ring seal 21.

Upper end section or cap 13, as seen in FIGS. 1 and 3 is provided with protruding section 22 which extends into body section 10 of the housing in a tight fit relation, and three passageways 23, 24 and 25 extend therethrough, each passageway being threaded at 26 for connection to a pipe, tube or conduit, not snown. The inner surface 27 (see FIG. 3) of protruding section 22 is provided with a plurality of radially extending grooves or channels 28, eight in this embodiment, extending from passageway 24 to the circular groove 20 (see FIG. 3) at the periphery of protruding section 22 and function as a sample fluid distributor as described below.

A first or outer cylindrical porous frit 29 having plurality of longitudinally extending spaced grooves or channels 30 on the outer surface thereof, eight in this embodiment, is positioned within body section 10 of the housing, in a tight fit relationship (see FIG. 1 and 2). A second or inner cylindrically configured porous frit 31 is located within and spaced from the first frit 29, porous frits 29 and 31 being positioned in a coaxial relation.

A cylindrical solid core or member 32 is positioned within the second frit 31 in a tight fit relation and includes a reduced diameter threaded end section 33 (see FIGS. 1, 2 and 4) which is secured in a threaded aperture 34 in the lower end section or cap 14. Core 32 is provided with a plurality of longitudinally extending grooves or channels 35 (four in this embodiment), a central passageway 36 in section 33 thereof, and a plurality of radially extending openings 37 (four in this embodiment) connecting grooves 35 with passageway 36, which function as a fluid component collection channel, as described hereinbelow.

Lower end section or cap 14 is provided with a protruding section 38 which extends into body section 10 of the housing in a tight fit relation. Protruding section 38 is provided with a centrally located counter-sunk portion 39 into which the lower ends of inner frit 31 and central core 32 extend in a tight fit relation, with threaded aperture 34 extending from central portion 39 through end section 4 for connection to an associated conduit, pipe, or tube, not shown.

A support plate or member 40 having a central counter-sunk portion 4 is positioned in abutting relation with protruding section 22 of upper end section or cap 13 and is located within outer frit 29 such that the upper ends of inner frit 31 and central core 32 extend into the counter-sunk portion 41 in a tight fit relation. Plate 40 is provided with an annular groove 42 in which is retained an O-ring seal 43 to prevent leakage between plate 40 and outer frit 29. Plate 40 may be glued, welded or otherwise bonded to section 22 which contains the radial distribution grooves or holes 28.

With the components of the column thus far described and assembled as shown in FIG. 1, a space is defined between frits 29 and 31, plate 40 and section 38 of end section or cap 14 and which contains a bed 44 of selected separating material or medium. The medium may, for example, be inserted, pumped or injected into the space in the form of a slurry or a dry form via passageway 25 connected via thread 26 to an external supply of the medium. As the medium is injected into the space to form the bed 44, air is discharged through passageway 23 to prevent entrapping and thus eliminating any dead volume within the column. The passageway 25 may be plugged after the medium has been injected using conventional means such as a valve, secured in the threads 26.

In the operation of the embodiment illustrated in FIG. 1, and with the grooves 28 in alignment and in fluid communication with grooves 30, a sample fluid to be chromatographically separated is directed into passageway 24 of end section 13 (see flow arrows) and through grooves 28 and into grooves 30 of outer porous frit 29, in a horizontal (inward radial flow) direction through frit 29 along the length thereof and through bed 44 and inner frit 31 into collection grooves 35 of central core 32, whereafter, the fluid components are divided through openings 37 and passageway 36 to a point of collection. The operation of the column of FIG. 1 is similar to that of the columns described and claimed in the above referenced application in that the flow is horizontal across the bed 44 along the longitudinal length thereof. However, as pointed out above, because of the grooves or flow channels in the outer frit and the central core, the construction of the column has to be greatly simplified. Furthermore, as seen in FIG. 1, upon removal of either of end section or cap 14 or end section or cap 13, the frits 29 and 31 and the bed 44 are readily accessible.

While the end section or cap 13 and outer frit 29 are provided with eight (8) grooves or channels 28 and 30 and the solid core 32 is provided with four (4) grooves or channels, the number of grooves may be increased or decreased without departing from the scope of this invention, since the purpose thereof is to provide even distribution of the sample fluid across the bed 44 and along the length thereof in a horizontal flow direction. Furthermore, both the outer frit 29 and inner core 32 may be provided with several circular grooves along the length thereof, to further aid in the homogeneous application and collection of the sample.

Also, while the direction of fluid sample flow is in an inwardly horizontal (radial) direction, the apparatus of FIG. 1 can be readily modified to direct the sample fluid in an outwardly horizontal (radial) direction. This could be accomplished by directing the fluid sample through outlet passage 36 rather than inlet passage 24, or by redesigning the inlet fluid lo distributor grooves 28 and providing aligned passages in plate 44 so that the distributor grooves would direct the sample fluid into the grooves or channels 35 of central core 32, and plugging the outlet openings 37 in core 32 and providing appropriate collection means in fluid communication with grooves 30 of outer frit 29.

For the fluid streamlines to be truly horizontal through the material bed 44, the axial pressure drops in grooves or channels 30 and 35 should be the same. Since the flow rate is the same through porous frits 29 and 31, the same axial pressures in grooves or channels 30 and 35 may be achieved by providing the same total cross-sectional areas for both grooves or channels 30 and grooves or channels 35.

Figure 5A:
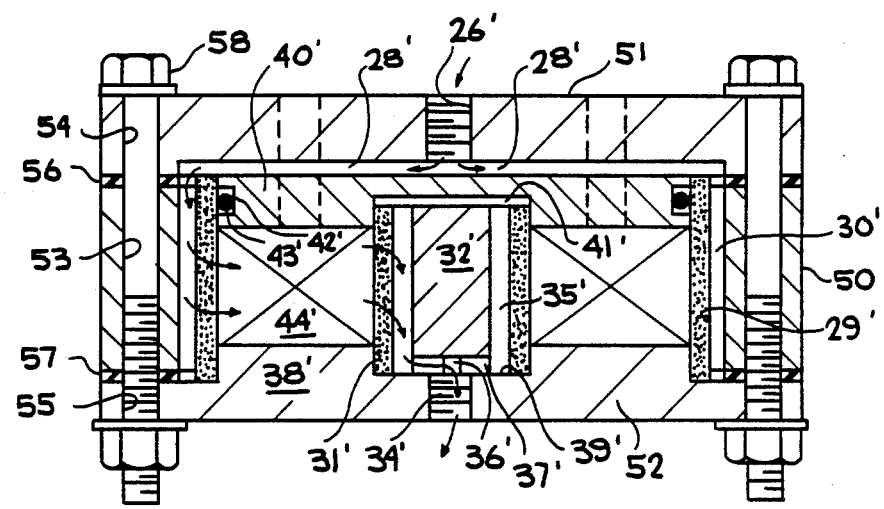
FIGS. 5A and 5B are cross-sectional views of other embodiments of the invention utilizing disposable horizontal flow beds and columns.

The embodiment of the invention illustrated in FIG. 5A is generally similar to that of FIG. 1 with respect to the construction of the fluid distributor, the outer and inner porous frits, the solid core members, and the support plate. Like components will be given corresponding reference numerals in the drawings, the differences in the two embodiments being primarily in the manner in which the components of the housing are removably secured, and the use of the disposable horizontal (radial) flow bed. The housing of FIG. 5A is composed of a cylindrical body section 50 and an upper end cap or section 51 and a lower end cap or section 52. Body section 50 is provided with a plurality of spaced openings or apertures 53 (only one shown in the drawing), while end caps 51 and 52 are provided with openings or apertures 54 and 55, respectively. which align with openings 53. A pair of annular seals or gaskets 56 and 57 having openings which align with openings 53 are positioned between body section 50 and end caps 51 and 52. Bolts 58 (only one shown) extend through openings 53, 54 and 55 and gaskets 56 and 57 for securing the housing components 50, 51 and 52 together.

End cap 51 is provided with a threaded fluid inlet passage 26' which directs fluid to a plurality of distributor grooves or channels 28' (only two shown) which are in alignment with longitudinally extending grooves or channels 30' in outer porous frit 29'. An inner porous frit 31' is snugly positioned around a solid core or member 32' having longitudinally extending grooves or channels 35'. The solid core 32' is secured to end cap 52 via a threaded end portion 33' secured in threaded passageway 34'. The grooves 35' of core 32' are connected to an outlet or collection passage 36' in end section 33' by a plurality of openings 37'.

A support plate 40' having a central counter-sunk portion 41' and an annular groove 42' for retaining O-ring 43' is positioned to cooperate with outer frit 29' and with inner frit 31' and solid core 32', as described earlier in the embodiment of FIG. 1. End cap 52 is provided with a protruding section 38' which includes a counter-sunk portion 39' into which ends of frit 31 and core 32 are positioned, as in the embodiment of FIG. 1. A bed 44' of selected separation medium is located between frits 29' and 31'.

The operation of the column of FIG. 5A is the same as described above with respect to the column of FIG. 1. However, the column of FIG. 5A is designed for ready replacement of disposable separation bed material, and for smaller (analytical) applications.

The means illustrated for securing the housing sections 50, 51 and 52 together may be replaced by counter-sunk screws, for example, that extend through end caps 51 and 52 into threaded openings in body section 50 so that the surface of the securing means would be flush with the outer surface of the end caps, thus allowing stacking of the columns. Stacking of the columns would allow for the collection (output) material from an upper column to be utilized as an input sample for the next lower column for further separation of the various components in the sample fluid. For example, the material of the bed of each subsequent column may be selected to separate and remove only a certain or specific component from the original sample fluid, each desired component being separated and removed (or siphoned off) as the fluid passes through the sequence of beds. Alternatively, means such as T-joints or taps, may be provided, if desired, between different stages of the stack of columns to siphon off or tap eluted material selectively from one or more columns before it is fed into the next lower or adjacent column.

Figure 5B:
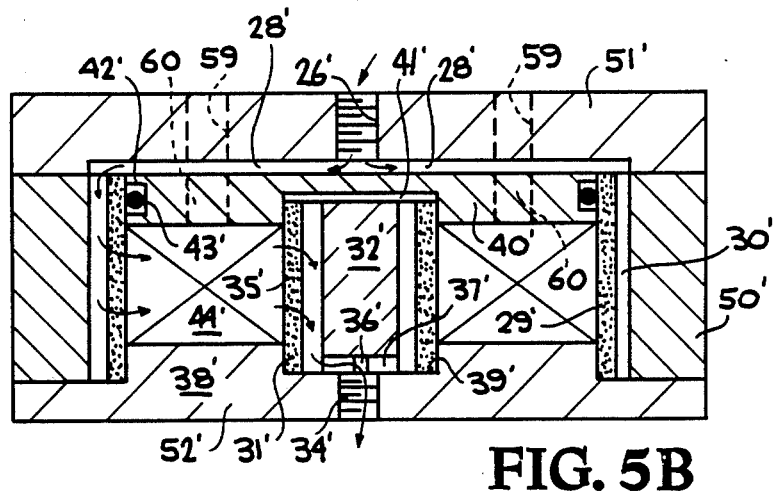

FIG. 5B illustrates an embodiment which is generally similar to the column shown in FIG. 5A, the principal difference being in the manner of securing the housing components together to make the entire column and housing, with the separation material prepacked therein, disposable. The column of FIG. 5A provides for removability of the porous frits and/or the separation material while in the embodiment of 5B, the housing components are made of selected materials and are fabricated to be integral or sealed (glued, bonded or molded) together, whereby the entire column together with the housing components are rendered disposable. Like components or components similar to those of FIG. 5A are given corresponding reference numerals.

In FIG. 5B, the housing is composed of a cylindrical body section 50', an upper end cap or section 51', and a lower end cap or section 52'. The end caps 51' and 52' are constructed so as to be in abutting relation with body section 50' and are secured together such as by welding, bonding, glueing, molding and the like, thereby eliminating the O-ring 43', gaskets 56, 57 and bolts 58 of the embodiment of FIG. 5A. This construction also eliminates a great deal of machining requirements, thereby reducing the cost of fabrication considerably. The remainder of the column of FIG. 5B is the same as that of FIG. 5A except that the upper end cap 51' and plate member 40' are provided with a pair of spaced and aligned apertures 59 and 60, which allow for insertion of the separation medium to form a bed within the housing and for the removal of any air trapped within the housing, as described above in the case of the embodiment illustated in FIG. 1.

The operation of the column of FIG. 5B is substantially the same as for the embodiment of FIG. 5A, the difference being in that the entire column of FIG. 5B is disposable after use. The column housing of the embodiment of FIG. 5B is constructed of inexpensive material, and the components 50' and 51' or 52' may also be integrally molded with the other end cap (51' or 52') being bonded or glued. Thereafter, the porous frits and core member are positioned within the housing, the separation bed material between the frits being injected through one of the openings or apertures 59-60, with air being removed through the other opening 59-60. The openings 59 and 60 are sealed (as by gluing or bonding etc) during the operation of the column.

The materials utilized in the illustrated embodiments of the improved chromatography column may be the same as those described in the above-referenced copending application. For example, the column housing and other non-filtering components may be constructed of material capable of withstanding extreme solvent and temperature conditions, such materials including but not limited to stainless steel, aluminum, titanium, glass, teflon, polycarbonate, polysulfone, polypropylene and the like. Similarly, the porous frits may be made of polyvinylidene fluoride (PVDF), polypropylene, teflon, stainless steel, polyacetate, polyester, polycarbonate, ceramics, and other porous materials. The separation bed material or medium may be composed of any material that is known and/or employed in the art of chromatographic separation.

It has been shown that the invention provides:
(1) elimination of any dead volume,
(2) easy bed packing and removal of trapped air,
(3) capability for HPLC application,
(4) simplified fluid distribution and collection arrangement which reduces the possibility of plugging up the system and provides for ready and easy cleaning,
(5) a simplified and less cumbersome construction and
(6) an optional, disposable construction.

It has thus been shown that the present invention provides an improved chromatography column, utilizing horizontal flows through the separating medium bed, which overcomes the problems associated with large diameter columns, while enabling scale-up to accommodate the demand for high volume, high resolution fluid separation in both preparative and analytical applications. One embodiment provides for a stacked column arrangement. Thus, the present invention provides a substantial advance in the state of this art.

The foregoing description of the preferred embodiments of the invention have been presented for purposes of illustration and description and for a better understanding of the invention. It is not intended to be exhaustive or to limit the invention to the precise form disclosed; and obviously, many modifications and variations are possible in light of the above teaching. The particular embodiments were chosen and described in some detail to best explain the principles of the invention and its practical application to thereby enable others skilled in the relevant art to best utilize the invention in various embodiments and with various modifications as are suited to the particular use contemplated. It is intended that the invention be defined by the claims appended hereto.

What is claimed is:

1. A chromatography column utilizing horizontal flow of sample material passing therethrough comprising:
a housing defining a chamber therein and including at least one removable end section,
a pair of longitudinally extending porous frits positioned in spaced relation with said chamber of said housing,
a bed of chromatographic separation material positioned in said chamber of said housing and intermediate said pair of porous frits,
one of said porous frits being adjacent said housing and provided with a plurality of longitudinally extending grooves on an outer surface thereof to define an inlet channel, another of said porous frits being positioned adjacent a core member having a plurality of longitudinally extending grooves to define an outlet channel, distribution means operatively connected to said inlet channel, collector means operatively connected to said outlet channel, said distribution means and said inlet channel being constructed to direct associated material to be separated in said bed evenly across a longitudinal length of said bed in a substantially horizontal direction.

2. The apparatus of claim 1, wherein said plurality of porous frits are coaxially positioned with respect to one another, said one porous frit having a larger cross-section than said another porous frit, and wherein said core member is centrally located in said housing chamber.

3. The apparatus of claim 2, wherein said core member is provided with a centrally located passage at one end thereof and a plurality of openings extending from said centrally located passage to said grooves defining said outlet channel.

4. The apparatus of claim 1, wherein said distribution means is incorporated into said removable end section of said housing and includes an inlet passage connected to a plurality of distribution channels which are connected to said grooves in said one porous frit defining said inlet channel to provide even distribution of associated material to said inlet channel.

5. The apparatus of claim 1, wherein said removable end section of said housing includes:

an end cap removably secured to a body section of said housing, and a plate located intermediate said end cap and said bed of chromatographic separation material, said plate being constructed to retain said bed intermediate said pair of porous frits.

6. The apparatus of claim 1, wherein said housing includes a body section and two removable end sections, and means for removably connecting each of said end sections to said body section.

7. The apparatus of claim 6, wherein said body section includes a flange on each end thereof, and wherein removable connecting means are located in the periphery of each of said end sections and are connected to an associated flange of said body section.

8. The apparatus of claim 6, wherein said body section of said housing is of a cylindrical configuration, and wherein each of said removable end sections includes a protruding portion which extends into associated ends of said body section.

9. The apparatus of claim 8, wherein said protruding portion of at least a second of said removable end sections is provided with a centrally located counter sunk portion into which an end of each of said another of said porous frits and said core member extend.

10. The apparatus of claim 9, wherein said protruding portion is provided with a threaded passageway, and wherein said core member is provided with a reduced cross-section end portion thread to cooperate with said threaded passageway for securing said core member to said second of said removable end sections.

11. The apparatus of claim 9, wherein said core member is provided with a passageway extending into one end thereof, and a plurality of openings extending from said passageway to said plurality of grooves in said core member.

12. The apparatus of claim 8, additionally including a plate member located adjacent said one removable end section of said housing and provided with a centrally located counter sunk portion into which an opposite end of each of said another of said porous frits and said core member extend.

13. The apparatus of claim 12, wherein said plate member is at least partially positioned within one end of said one of said porous frits.

14. The apparatus of claim 12, wherein said one of said removable end sections and said plate member are each provided with a pair of spaced apart and aligned passages, whereby chromatographic separation material can be passed through a first of said aligned passages into said chamber and air within said chamber can be discharged through a second of said aligned passages.

15. The apparatus of claim 6, additionally including seal means located intermediate said body section and said two removable end sections.

16. In a chromatographic column having a housing defining a chamber therein and a pair of removable end sections, a pair of porous frits positioned in spaced coaxial relation within said chamber, a core member located within a first of said pair of porous frits, and a bed of chromatographic separation material positioned in said chamber intermediate said pair of porous frits, the improvement comprising:

a second of said pair of porous frits being provided with a plurality of grooves on an outer surface extending along a longitudinal length of said second frit, said core member being provided with a plurality of grooves on an outer surface and extending along a longitudinal length thereof, a first of said pair of removable end sections being provided with a fluid distribution means including a passage connected to a plurality of radially extending grooves, said grooves being positioned to provide fluid communication with said grooves on said second porous frit, a second of said pair of removable end sections being provided with a passage therethrough, said passageway being in fluid communication with said grooves on said core member.

17. The chromatographic column of claim 16, wherein said second of said removable end sections includes a threaded portion secured to a threaded end section of said core member.

18. The chromatographic column of claim 17, wherein said core member includes a passage extending into one end thereof, and a plurality of openings interconnecting said passage with said plurality of grooves on said core member.

19. The chromatographic column of claim 16, wherein said second of said removable end sections of said housing includes a centrally located counter sunk portion, one end of said first of said pair of porous frits and said one end of said core member each extending into said counter sunk portion.

20. The chromatographic column of claim 16, additionally including a plate located adjacent said first of said pair of removable end sections, said plate including a counter sunk portion, an opposite end of said first of said pair of porous frits and an opposite end of said core member each extending into said counter sunk portion of said plate.

21. The chromatographic column of claim 20, wherein said plate is positioned at least partially within one end of said second of said pair of porous frits.

22. The chromatographic column of claim 16, wherein said first of said pair of removable end sections of said housing is provided with a pair of spaced apart openings extending therethrough, a first of said openings being adapted to provide for passage of chromatographic separation material inwardly through said first of said removable end sections into said chamber, a second of said openings being adapted to provide for passage of air from said chamber outwardly through said first of said removable end sections.

23. The chromatographic column of claim 16, additionally including seal means located intermediate each of said removable end sections of said housing and an associated end of a body section of said housing.

24. The chromatographic column of claim 23, wherein said second of said pair of porous frits is positioned in a close fit relation to an inner surface of said body section of said housing, and wherein said first of said pair of porous frits is positioned in a close fit relation to said outer surface of said core member.

* * * * *